US00PP36932P2

(12) United States Plant Patent
Fell

(10) Patent No.: US PP36,932 P2
(45) Date of Patent: Sep. 2, 2025

(54) ***ALOCASIA* PLANT NAMED 'Dragon Wings'**

(50) Latin Name: ***Alocasia* hybrid**
Varietal Denomination: Dragon Wings

(71) Applicant: David Fell, Waimanalo, HI (US)

(72) Inventor: David Fell, Waimanalo, HI (US)

( * ) Notice: Subject to any disclaimer, the term of this patent is extended or adjusted under 35 U.S.C. 154(b) by 0 days.

(21) Appl. No.: 19/183,791

(22) Filed: Apr. 19, 2025

(51) Int. Cl.
*A01H 6/10* (2018.01)
*A01H 5/02* (2018.01)

(52) U.S. Cl.
USPC ..... Plt./373

(58) Field of Classification Search
USPC ..... Plt./373
CPC ..... A01H 6/10; A01H 5/02; A01H 5/12
See application file for complete search history.

*Primary Examiner* — Keith O. Robinson
(74) *Attorney, Agent, or Firm* — James R. Holm; Plant Novelty Rights, LLC

(57) ABSTRACT

A new and distinct variety of *Alocasia* plant named 'Dragon Wings', particularly distinguished by large plant size, large and broad-sized leaves, distinct dark purplish grey leaf coloration with tints of yellow green on the adaxial surface and distinct purplish red coloration on the abaxial surface, and hybrid vigor.

4 Drawing Sheets

Figure 1:
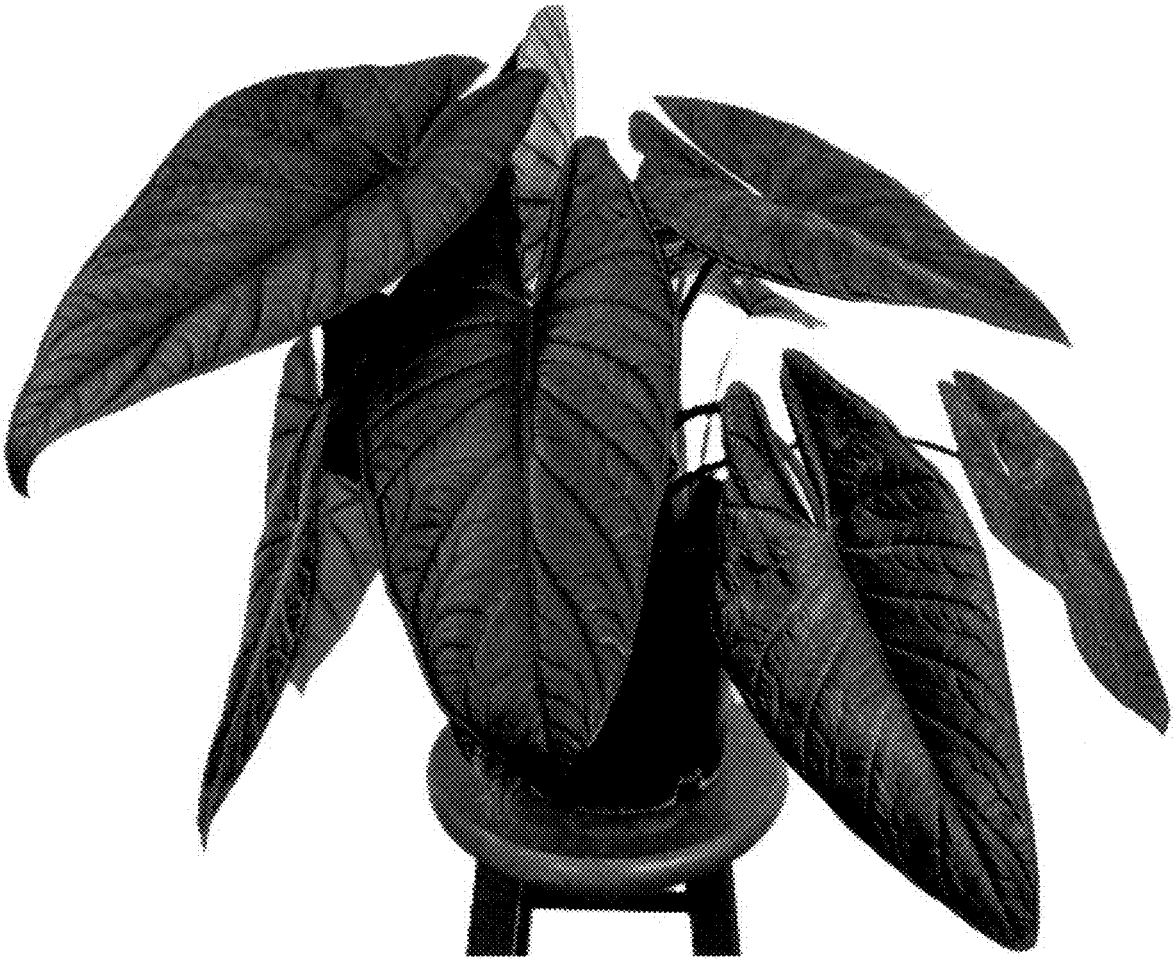

Genus and species: *Alocasia* hybrid.
Variety denomination: 'Dragon Wings'.

BACKGROUND OF THE NEW PLANT

The present invention comprises a new and distinct interspecific hybrid plant of *Alocasia,* hereinafter referred to by its cultivar name 'Dragon Wings'.

The new cultivar was derived from a breeding program conducted by the inventor at a nursery in Waimanalo, Hawaii. The overall purpose of the breeding program is to create new *Alocasia* plants with unique foliage that are durable with a good growth rate and disease and pest resistance. 'Dragon Wings' is the product of a controlled cross made by the inventor in February 2021 between the *Alocasia baginda* plant named 'Dragon Scale' (unpatented) as the female parent and an unnamed and unpatented *Alocasia scalprum* plant as the male parent. 'Dragon Wings' was selected in Waimanalo, Hawaii by the inventor in November 2021 as a single unique plant from amongst progeny plants derived from said cross.

The new cultivar was selected based on its increased vigor compared to the parent plants, large leaf size, large plant size and distinctive leaf colorations. 'Dragon Wings' was first reproduced asexually by vegetative rhizome divisions in February 2022 in Waimanalo, Hawaii. Asexual propagation by vegetative rhizome divisions of the new cultivar has shown that the unique features of the new cultivar are stable and reproduce true-to-type through four successive generations.

STATEMENT REGARDING PRIOR DISCLOSURES BY THE INVENTOR

The Inventor asserts that no publications or advertisements relating to sales, offers for sale, or public distribution occurred more than one year prior to the effective filing date of this application. Any information about the claimed plant would have been obtained from a direct or indirect disclosure from the Inventor. The Inventor claims a prior art exemption under 35 U.S.C. 102 (b) (1) for disclosures and/or sales that fall within a one-year grace period prior to the filing date.

SUMMARY OF THE INVENTION

The new *Alocasia* cultivar has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Alocasia* cultivar. The combination of these characteristics distinguishes 'Dragon Wings' as a new and distinct variety of *Alocasia:*

1. Large plant size;
2. Large and broad-sized leaves;
3. Distinct dark purplish grey leaf coloration faintly tinted with yellow green on the adaxial surface and distinct purplish red coloration on the abaxial surface; and
4. Hybrid vigor.

The new *Alocasia* cultivar 'Dragon Wings' can be distinguished from its male and female parents by having larger and broader leaves and a larger plant size. 'Dragon Wings' has darker purplish grey leaf coloration with tints of yellow green on the adaxial surface compared to the lighter adaxial surface leaf coloration of the male and female parents. 'Dragon Wings' is more vigorous when compared to the lower vigor of its male and female parents. When compared to plants of the species *Alocasia scalprum,* which is sold commercially under the common name 'Samar Lance' (unpatented), 'Dragon Wings' has a broader leaf size and darker purplish grey colored leaves with faint tints of yellow green on the adaxial surface.

DESCRIPTION OF THE PHOTOGRAPHS

The new *Alocasia* cultivar is illustrated by the accompanying-colored photographs which show the overall appearance and distinct characteristics of the plant. The colors shown are as true as can be reasonably obtained by conventional photographic procedures. The photographs are of a 4-month old plant grown in an 8-inch container in a shade house in Waimanalo, Hawaii under 73 percent shade (approximately 4800-foot candles) with a temperature range of 60 to 90 degrees Fahrenheit and a humidity range of 40 to 80 percent. Colors in the photographs may differ slightly from the color values cited in the botanical description which accurately describes the colors of the new variety.

FIG. 1. shows a side view of the overall plant form and foliage of 'Dragon Wings'.

Figure 2:
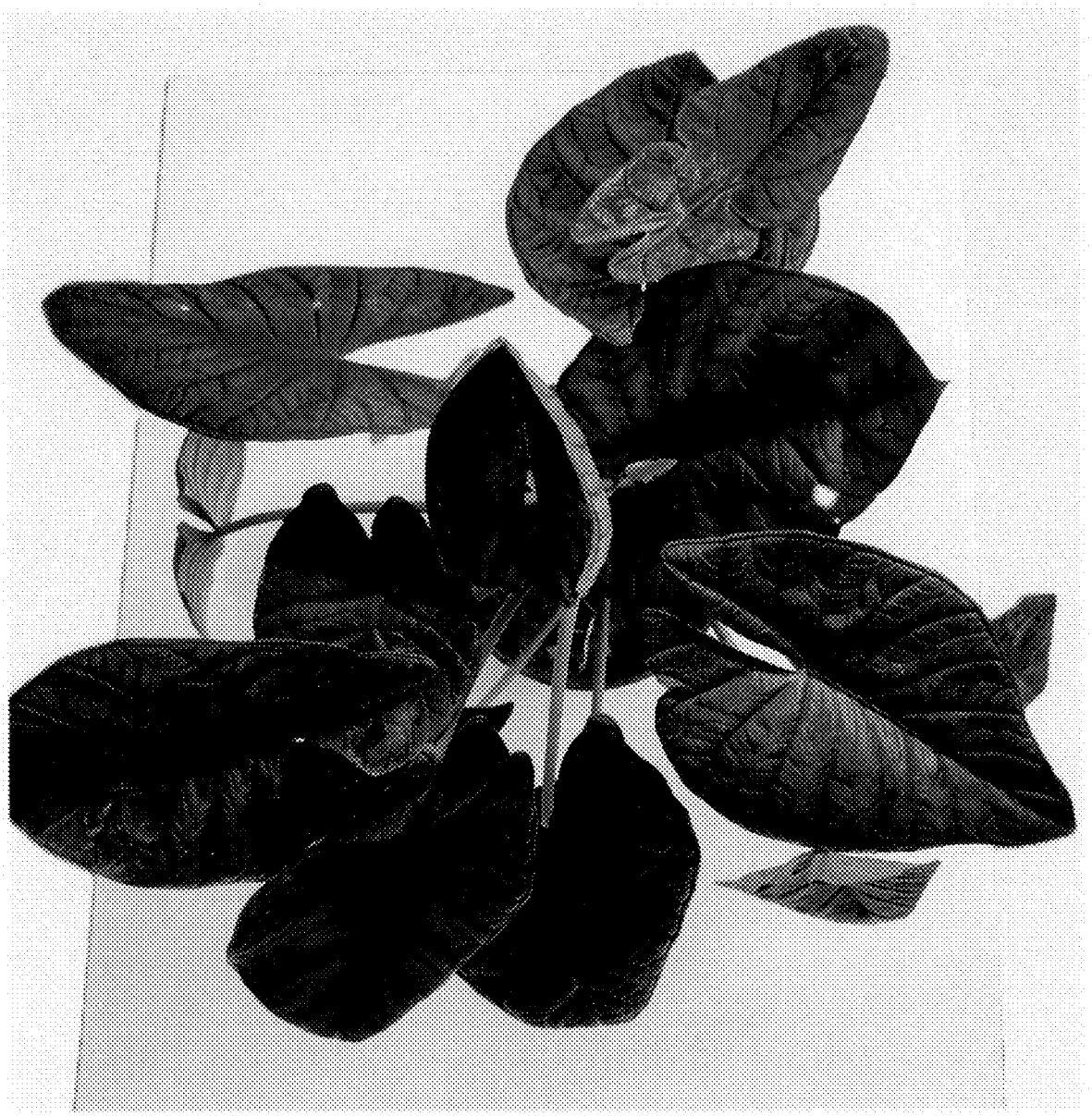

FIG. 2. shows a top view of the overall plant form and foliage of 'Dragon Wings'.

Figure 3:
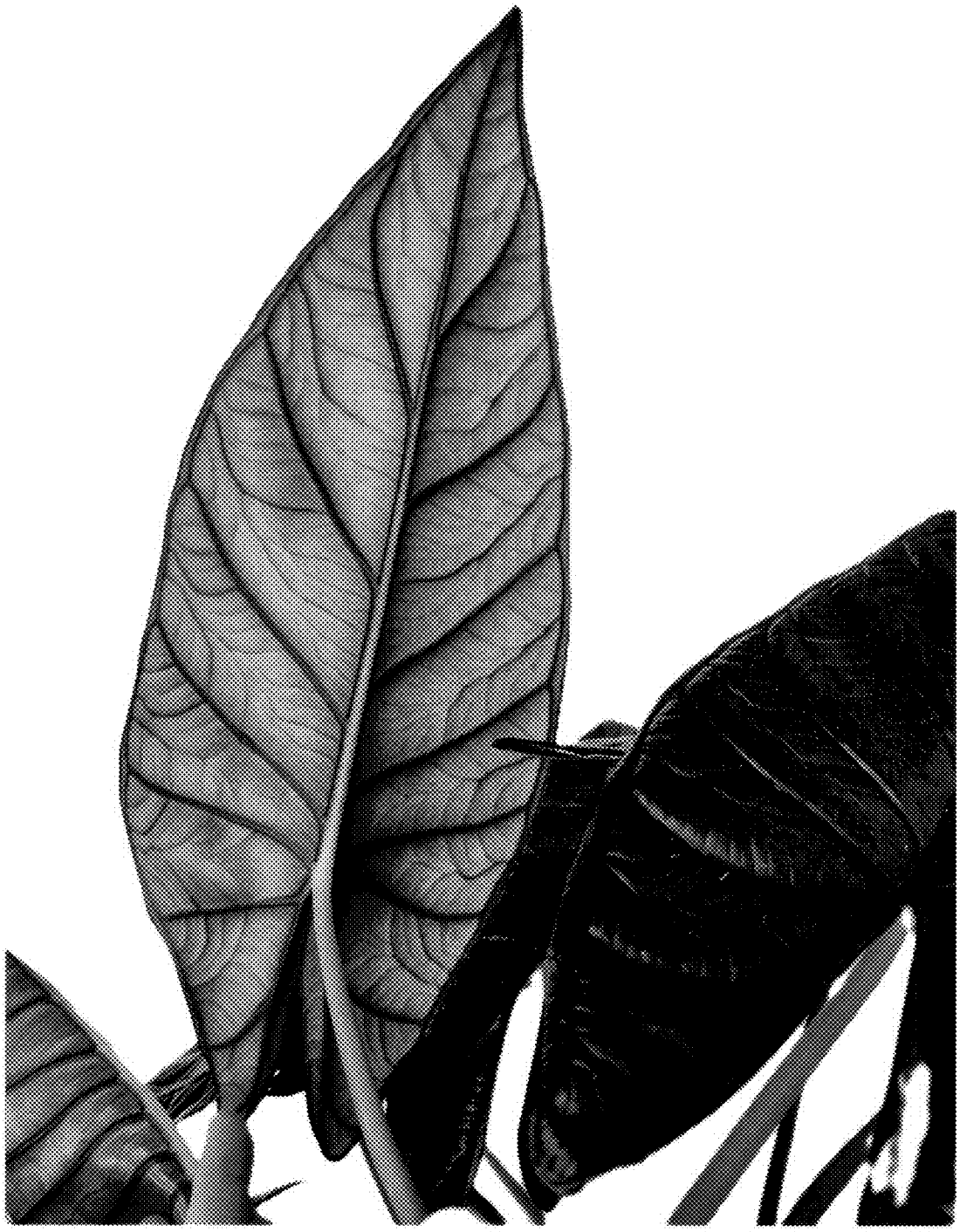

FIG. 3. shows a closeup of the abaxial surface of a mature leaf of 'Dragon Wings'.

Figure 4:
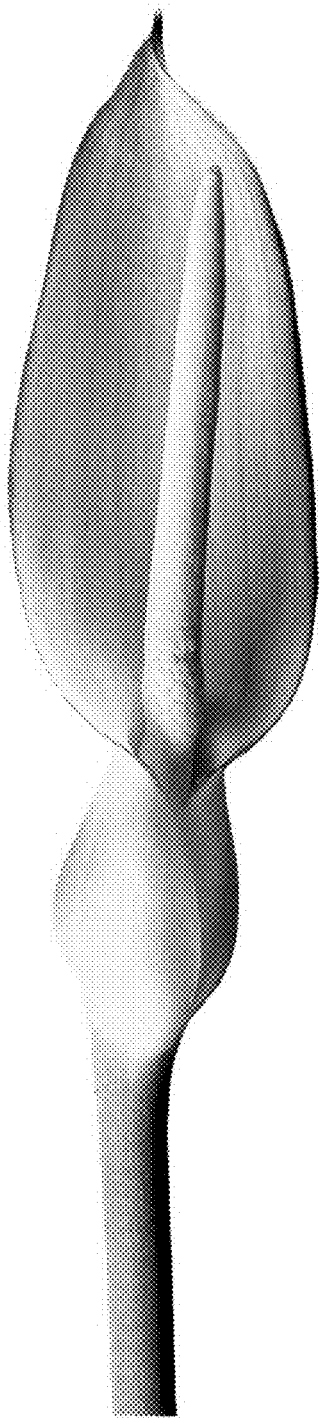

FIG. 4. shows the typical inflorescence observed on plants of 'Dragon Wings'.

DESCRIPTION OF THE NEW VARIETY

In the following description, color references are made to The Royal Horticultural Society Colour Chart, Sixth Edition, except where general color terms of ordinary dictionary significance are used.

The following observations and measurements describe plants grown under 73 percent shade (approximately 4800-foot candles) in a shade covered greenhouse in Waimanalo, Hawaii. Detailed descriptions were taken in March 2025 from a 4-month-old plant grown in an 8-inch container. Measurements and numerical values represent averages of typical plant types.

DETAILED BOTANICAL DESCRIPTION

Classification:

*Family*.—Araceae.

*Botanical*.—*Alocasia* hybrid.

*Common*.—*Alocasia* or Elephant Ear.

*Denomination*.—'Dragon Wings'.

General description:

*Plant type*.—Rhizomatous tropical perennial.

*Plant habit*.—Upright with one primary (dominant) rhizomatous branch, few secondary branches.

*Height from soil level to top of foliar plane*.—Approximately 35.0 cm.

*Plant spread*.—Approximately 77.0 cm.

*Number of secondary branches*.—1 observed.

*Branching characteristics*.—Primary branch is approximately 4.5 cm in diameter at the base above the soil level; secondary branch is approximately 3.0 cm in diameter above the soil level.

*Growth rate*.—Medium to Fast.

*Propagation type*.—Vegetative rhizome divisions and meristem tissue culture.

*Roots*.—Thick, fleshy and fibrous, colored 155D (yellowish white).

Foliage description:

*Quantity of leaves per branch*.—Primary branch: 9. Secondary branch 7.

*Arrangement*.—Alternate to spiraled.

*Attachment*.—Petiolate.

*Division*.—Simple.

*Cataphylls*.—General description: Cataphylls are not persistent and are only observed on pre-emergent leaves; cataphylls wither and become brown and desiccated within a few days of juvenile leaf emergence. Length: 14.0 cm. Width: 3.0 cm at the base then narrowing to 1.5 cm at 1.0 cm below the apex of the cataphyll. Shape: Lanceolate. Texture and luster: Inner surface: Smooth, glabrous and shiny. Outer surface: Corrugated, glabrous and matte. Color: Inner surface: 157C (pale yellow green) to 157D (greenish white). Outer surface: 160B (light yellow) to 160C (pale greenish yellow).

*Lamina*.—Shape: Broadly sagittate. Length: Approximately 35.0 cm to 40.0 cm when measured along the center axis of the foliar plane. Width: Approximately 16.0 cm to 20.0 cm at the widest point above the lobes. Orientation: Initially held vertically and becoming pendulous when mature. Appearance: Incised venation on the adaxial surface with bullate leaf tissue between the venation. Apex: Aristate on immature leaves then becoming obtuse to slightly cuspidate on mature leaves. Base: Sagittate. Lobes: Length: About 10.0 cm to 11.0 cm when measured from the apex of the sinus to the base of the lobe. Width: About 8.0 cm to 9.0 cm when measured at the apex of the sinus across to the edge of the lamina. Margins: Entire. Texture and luster: Juvenile foliage: Abaxial surface: Slightly rugose, glabrous and glossy. Adaxial surface: Rugose, glabrous and glossy. Mature foliage: Abaxial surface: Slightly rugose, glabrous and matte. Adaxial surface: Rugose, glabrous and satiny. Venation pattern: Pinnate, one primary vein (midvein) and approximately 18 secondary veins with numerous veinlets appearing in a netted pattern. Color: Juvenile foliage, adaxial surface: Interveinal areas: 139A (dark yellowish green) flanking the secondary veins with areas of N144A (strong yellowish green) centered between the secondary veins. Primary vein: 139A (dark yellowish green). Secondary veins: 139A (dark yellowish green). Veinlets: 139A (dark yellowish green). Juvenile foliage, abaxial surface: Interveinal areas: 186C (dark purplish pink) flanking the secondary veins with a lighter area 62C (light purplish pink) centered between the secondary veins. Primary vein: 145C (light yellow green) turning to N77A (greyish purple) towards the apex. Secondary veins: N77A (greyish purple). Veinlets: N77B (greyish purplish red). Mature foliage, adaxial surface: Interveinal areas: N186A (dark purplish grey) and faintly tinted with 146B (moderate yellow green). Basal notch: Inconspicuous. Primary vein: N186A (dark purplish grey). Secondary veins: N186A (dark purplish grey). Veinlets: N186A (dark purplish grey). Mature foliage, abaxial surface: Interveinal areas: 186B (moderate purplish red) to 186C (moderate purplish pink). Primary vein: 146D (moderate yellow green) from the base to near the center then streaked with N77A (greyish purple) through the center before becoming solid N77A (greyish purple) towards the apex. Secondary veins: N77A (greyish purple). Veinlets: N77B (greyish purplish red).

*Petioles*.—Strength: Flexible. Aspect: Initially held upright and then arching downwards with development. Length (mature leaves): Approximately 34.0 cm. Diameter (mature leaves): Distally: 0.6 cm at point of attachment to the lamina. Proximally (above wing apex): 1.0 cm. Texture and luster: Juvenile leaves: Smooth, glabrous and shiny. Mature leaves: Smooth, glabrous and matte. Color: Juvenile leaves: 145A (strong yellow green). Mature leaves: 137B (moderate olive green). Wings: Length: Approximately 7.0 cm to 9.0 cm. Width: Approximately 3.5 cm at the base. Color: Juvenile leaves: Outer surface is 145A (strong yellow green), inner surface is not visible. Mature leaves: Outer surface is 137B (moderate olive green), inner surface is 157C (pale yellow green) to 157D (greenish white).

Inflorescence:

*Type*.—Spadix surrounded by a spathe, male portion held above female portion.

*Peduncle*.—Length: 13.0 cm. Diameter: 1.4 cm, widening towards the base of the spadix, 2.0 cm. Color: 143C (strong yellow green).

*Spath*.—Shape: Wedge-shaped above female zone, elliptic surrounding female zone. Margin: Entire. Length: 9.5 cm above female zone, 3.5 cm surrounding female zone. Color: Above female zone: Outer surface: 150C (yellow green), with tints 187B to 187C (dark red) along the margin. Inner Surface: 150C to 150D (yellow green). Surrounding female zone: 150C (yellow green).

*Spadix*.—Length: 9.8 cm. Appendix zone: Shape: Lanceolate. Apex: Obtuse. Length: 4.7 cm. Width: 1.0 cm. Color 158A to 158B (pale yellow). Male Zone: Shape: Cylindrical. Length: 2.7 cm. Width: 1.0 cm. Color: NN155A (yellowish white). Female zone: Shape: Conical. Length: 2.4 cm. Width: 1.6 cm. Color: 143B (strong yellow green).

Cold tolerance: None observed.

Disease and pest tolerance: Resistant to two-spotted spider mite (*Tetranychus urticae*).

Fruit and seed set: None observed to date.

Drought tolerance: None observed.

What is claimed is:

1. A new and distinct variety of *Alocasia* plant named 'Dragon Wings', substantially as illustrated and described herein.

* * * * *